United States Patent [19]

Marino

[11] Patent Number: 4,758,155
[45] Date of Patent: Jul. 19, 1988

[54] DENTAL ARTICULATOR MOUNT

[76] Inventor: Joseph A. Marino, 82 Gladstone St., East Boston, Mass. 02128

[21] Appl. No.: 858,722

[22] Filed: May 2, 1986

[51] Int. Cl.$^4$ .............................. A61C 11/00
[52] U.S. Cl. ........................ 433/58; 433/54; 433/61
[58] Field of Search .............. 433/54, 57, 58, 59, 433/61, 62, 64; 248/362

[56] References Cited

U.S. PATENT DOCUMENTS

| 1,022,055 | 4/1919 | Weiss | 433/58 |
| 1,478,722 | 12/1923 | Wheeler . | |
| 1,840,400 | 1/1932 | Lebherz | 248/362 |
| 2,275,726 | 3/1942 | Burns et al. . | |
| 2,608,761 | 9/1952 | Scott | 433/58 |
| 3,159,370 | 12/1964 | Rubinstein | 248/362 |
| 3,908,271 | 9/1975 | Derda et al. | 433/58 |
| 4,047,302 | 9/1977 | Cheythey | 433/56 |
| 4,189,837 | 2/1980 | Stele | 433/57 |
| 4,500,289 | 2/1985 | Garganese et al. | 433/54 |

FOREIGN PATENT DOCUMENTS 658989 4/1938 Fed. Rep. of Germany ........ 433/54

OTHER PUBLICATIONS

Hanau Radial Shift Articulator Model 166-1 as applied to Full Denture Prosthodontics, 1981, Teledyne Hanau.
Hanau Radial Shift Articulator Model 166-1 as applied to Occlusal Reconstruction, 1981, Teledyne Hanau.

Primary Examiner—Randolph A. Reese
Assistant Examiner—Anthony Knight
Attorney, Agent, or Firm—Wolf, Greenfield & Sacks

[57] ABSTRACT

A mounting apparatus for a dental articulator including a stationary base, a rigid support member extending from the base and an upper clamp for releasably receiving and supporting the articulator upper member. An adjustable support piece is retained on the rigid support member and is adapted to contact the articulator lower member to limit the lowermost position thereof while permitting at least lateral movement of the articulator lower member relative to the articulator upper member to thus stimulate human jaw movements.

16 Claims, 2 Drawing Sheets

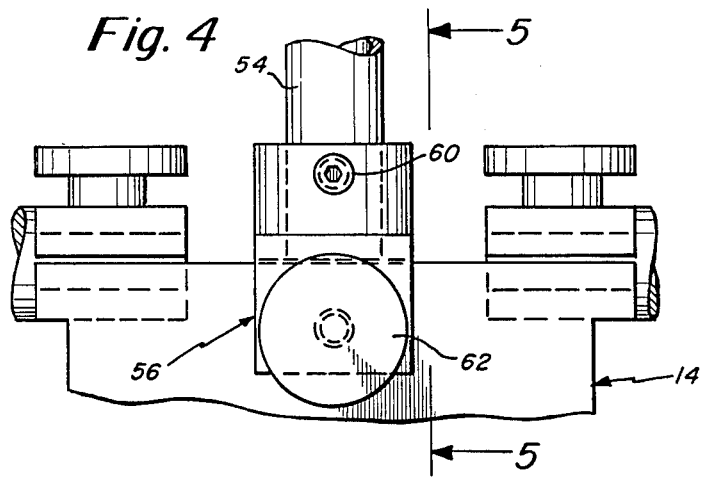
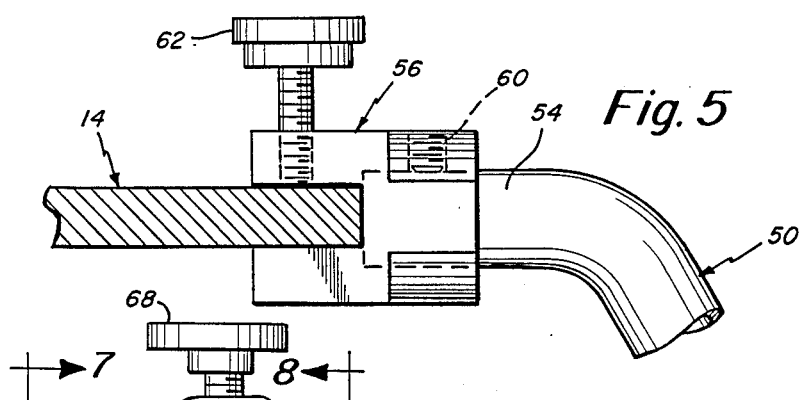
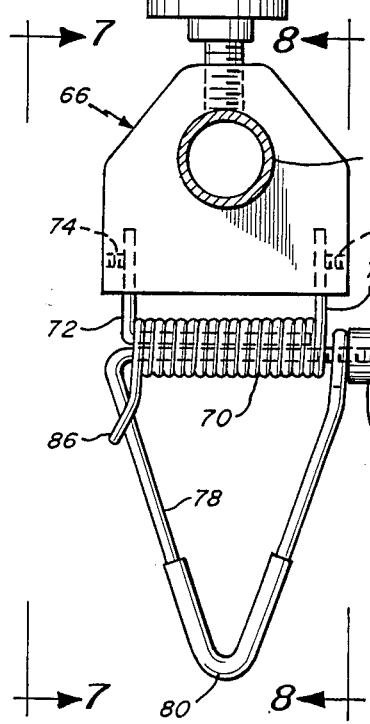
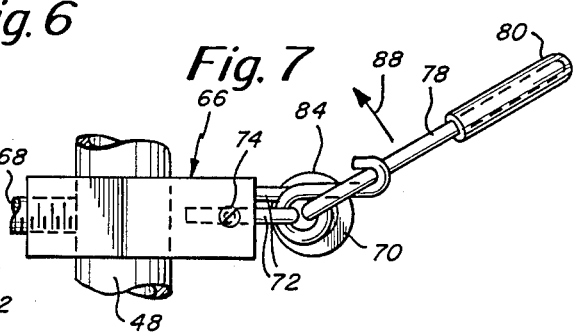
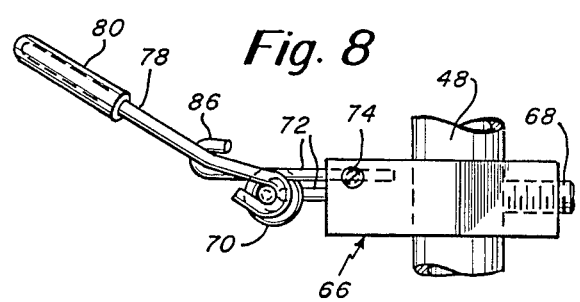

DENTAL ARTICULATOR MOUNT

BACKGROUND OF THE INVENTION

The present invention relates in general to a mounting apparatus for a dental articulator and pertains, more particularly, to a mounting apparatus that enables accurate duplication of the movement of the lower human jaw.

Dental articulators are well known in the prior art and are generally used for two purposes. First, as a diagnostic and planning instrument and second, for the technical procedures in constructing prostheses and other restorative appliances. Such restorative appliances typically include full upper and lower dentures, partial dentures, or complete mouth bridge work. In fact, all such restorative appliances are constructed on such dental articulators.

Typically, dental articulators are designed such that the upper half of the instrument, on which is mounted the upper dental arch cast, is movable laterally and back and forth in an attempt to duplicate the movements of the human jaw. These jaw movements which must be duplicated include the retruded contact position, the intercuspal position, as well as the protruded and lateral positions. However, in most of the prior art articulators, these movements of the human jaw are re-created or duplicated inaccurately. This results from the fact that the upper jaw member of the articulator is movable, and the lower jaw member is stationary, whereas in the human jaw, the reverse is true. That is, in the human jaw, the upper jaw is stationary, whereas the lower jaw experiences the protrusive and retrusive movement, as well as lateral movement, about the temporomandibular joint. Therefore, the restorative appliances which are constructed on such dental articulators simulate movement of the mouth in a manner opposite to the actual movement of the mouth so that all registrations are being transposed incorrectly, and the movements of the lower human jaw and the temporomandibular joints are recreated or duplicated inaccurately on such dental articulators.

It is known that the lower human jaw experiences protrusive and retrusive movement, as well as movement in lateral directions from a vertical axis which may be referred to as the centric axis. As the lower human jaw moves to either side of the centric axis, it is moving not only laterally but also downwardly with respect to the upper human jaw. This lateral and downward movement of the lower jaw is caused by the intercuspal engagement of the upper and lower posterior teeth. Accordingly, in order for a dental articulator to accurately duplicate human jaw movements, and in particular, the movement of the lower human jaw in the lateral direction, the articulator must be constructed to simulate all these directions of movement of the lower human jaw which include protrusive and retrusive movement and lateral movement, with the lateral movement being downwardly as the lower jaw moves laterally with respect to the centric axis.

Although prior art articulators have been developed in which the lower jaw portion is movable, these designs have generally speaking been relatively complex and require substantial modification to state-of-the-art articulators. In this connection refer to U.S. Pat. No. 4,047,302 to Cheythey and also U.S. Pat. No. 4,189,837 to Stele. In addition to being relatively complex in construction, and requiring total articulator redesign, the mechanisms employed in these articulators also do not accurately simulate all movements of the lower human jaw.

Accordingly, it is an object of the present invention to provide a mounting apparatus for a dental articulator which enables accurate duplication of the movement of the lower human jaw.

Another object of the present invention is to provide a mounting apparatus in accordance with the preceding object and in which the mounting apparatus is readily adapted for use with a state-of-the-art dental articulators.

A further object of the present invention is to provide a mounting apparatus that can be used with a standard dental articulator without requiring any substantial redesign of the articulator itself and to thus carry out in a very simplified manner a conversion from simulation of jaw movement by movement of the upper part of the dental articulator to instead provide for movement of the lower part of the dental articulator.

Still another object of the present invention is to provide a mounting apparatus for a dental articulator in which the mounting apparatus permits holding of the articulator in a number of different positions and furthermore enables use of the mounting apparatus with a variety of different types and forms of commercially available dental articulators.

SUMMARY OF THE INVENTION

To accomplish the foregoing and other objects, features and advantages of the invention there is provided a mounting apparatus for a dental articulator in which the articulator has an upper member for supporting an upper dental cast, a lower member for supporting a lower dental cast and pivot means to enable relative movement between the upper and lower members including protrusive, retrusive and lateral movements therebetween. The mounting apparatus of the invention comprises a stationary base, a rigid support member having a lower end supported from the stationary base and having an upper end, and a clamp means for releaseably receiving and supporting the articulator upper member. The clamp means is disposed at the upper end of the rigid support member is adapted to hold the articulator upper member in a stationary position relative to the base. The stationary base preferably has a swivel means for supporting the lower end of the rigid support member and in the disclosed embodiment has vacuum means to enable to the fixed securing of the base to a support surface. There is also preferably a base clamp for clamping the rigid support member in one of a number of different possible positions within the stationary base. The rigid support member is preferably of somewhat hook-shape with the stationary base disposed under the articulator lower member. The rigid support member has a lower end that is disposed angularly to the stationary base and has an upper end that is disposed substantially horizontally where attached to the clamp means. The rigid support member may be in the form of a support bar having a reversed curve section intermediate the ends. The support bar is preferably disposed at a rear of the articulator so that it does not interfer with the manipulation of the articulator. To provide support for the lower member of the articulator the mounting apparatus further comprises an adjustable support piece and means for supporting the adjustable support piece from the rigid support member intermediate the ends thereof. The adjustable support piece has means for contacting the articulator lower member to limit the lower most position thereof while permitting at least lateral movement of the articulator lower member relative to the articulator upper member to thus simulate human jaw movements. The means for supporting the adjustable support piece includes a support piece mount secured from the angularly disposed lower end of the rigid support member. The clamp means at the top of the mount may include a C-shaped piece for receiving the articulator upper member. Means are provided for releasably securing the clamp means to the articulator upper member. The adjustable support piece may comprise a support arm pivotly attached to the means for supporting the adjustable support piece. The support arm has an outer free end that contacts the underside of the articulator lower member. Means are provided for releasably securing the support arm in a fixed position.

In the use of the mounting apparatus of the present invention, it is noted that the upper member of the articulator is fixed in position and thus has substantially no movement other than adjustments in the position thereof. However, the articulator lower member may have its position controlled quite accurately by the adjustable support piece so as to place the lower dental cast in proper relationship to the upper dental cast. Then, by release of one or the other of the centric latches associated with the articulator the lower member (mandible) may then be readily moved protrusively, retrusively or laterally or relative to the articulator upper member (maxilla).

BRIEF DESCRIPTION OF THE DRAWINGS

Numerous other objects features and advantages of the invention should now become apparent upon a reading of the following detailed description taken in conjunction with the accompanying drawings, in which:

FIG. 4 is a fragmentary top plan view showing further details of the upper clamp of the mounting apparatus;

FIG. 5 is a cross-sectional view taken along line 5—5 of FIG. 4 showing further details of the upper clamp;

FIG. 6 is a cross-sectional view taken along line 6—6 of FIG. 3 showing further details of the adjustable support piece;

FIG. 7 is a side view of FIG. 6 taken along line 7—7 of FIG. 6; and

FIG. 8 is an opposite side view taken along line 8—8 of FIG. 6.

DETAILED DESCRIPTION

Figure 1:
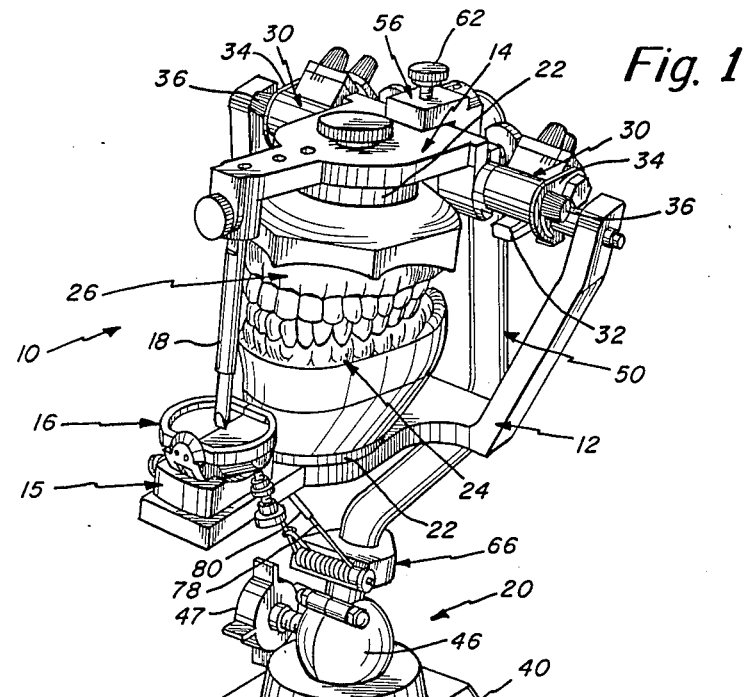
FIG. 1 is a perspective view of the mounting apparatus of the present invention employed in association with a state-of-the-art dental articulator.

Referring now to the drawings, there is illustrated generally at 10 a dental articulator being supported from a mounting apparatus generally identified at 20. The dental articulator that is described herein is a standard dental articulator and more specifically is a Hanau Radial Shift Articulator, model 166-1 produced by Teledyne Hanau of Buffalo N.Y. Because these articulators are of conventional design they are not described in complete detail herein, although, reference is made to primary parts of the dental articulator. For further details of the dental articulator construction reference may be made to instruction booklets pertaining to the device identified as Hanau Radical Shift Articulator model 166-1 as applied Occlusal Reconstruction and Hannau Radial Shift Articulator model 166-1 as applied to Full Denture Prosthodontics. These publications are both copyright 1981 Teledyne Hanau of Buffalo, N.Y., U.S.A.

The dental articulator comprises a lower member 12 and an upper member 14. The lower member 12 supports a rocker base 15 which in turn supports the adjustable incisal guide 16. Cooperating with the guide 16 is the incisal pin 18 which is supported from the upper member 14.

Both of the members 12 and 14 have associated therewith mounting plates 22. These mounting plates support dental arch casts identified in the drawings as lower or mandibular dental cast 24 and upper or maxillary dental cast 26.

Figure 2:
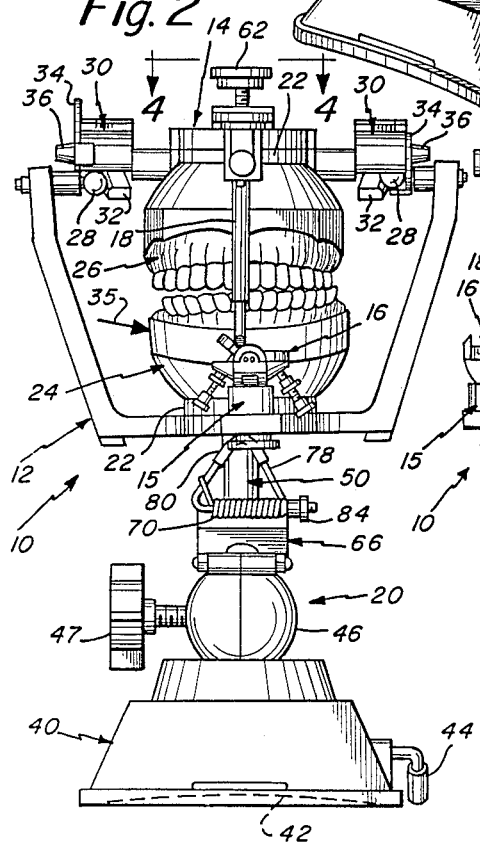
FIG. 2 is a front elevation view of the apparatus of FIG. 1 and illustrating a lateral excursion of the lower jaw cast relative to the stationary upper jaw cast.
Figure 3:
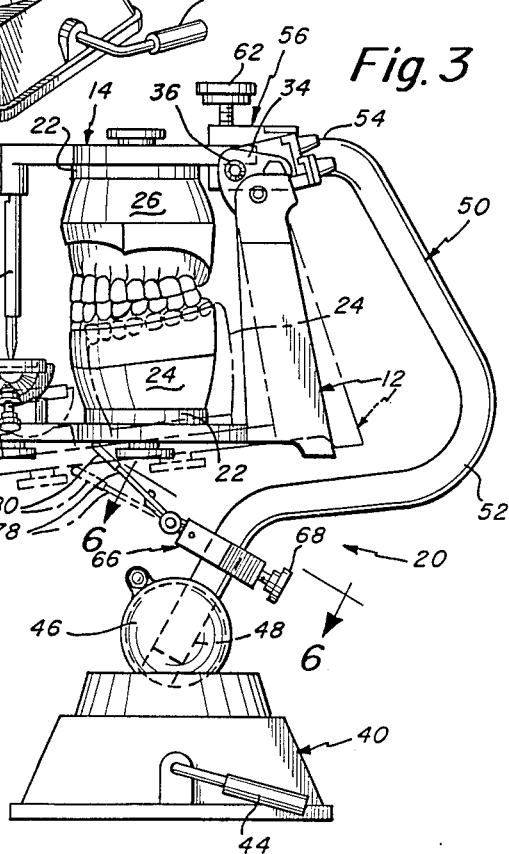
FIG. 3 is a side elevation view of the mounting apparatus and articulator of FIG. 1 and further illustrating the positioning of the articulator lower member by means of the adjustable support piece from the articulator mount.

The relative movement between the articulator lower member 12 and the articulator upper member 14 is carried out by means of cooperative engagement between condyles 28 and left and right condilar guides 30. FIGS. 1-3 also show the left and right Bennett angles 32. The drawings also show the left and right centric latches 34 along with their associated thumb screws 36 that may be used to secure and release the centric latches. In this regard in FIG. 2, it is noted that the centric latch 34 in the left of the view has been released so as to permit left lateral excursion of the lower jaw cast in the direction indicated by the arrow 35. Thumb pressure may be used to force the cast 24 in the direction indicated by the arrow 35 in FIG. 2. The movement of the lower member 12 in this regard is controlled by the mounting apparatus of the present invention and in particular by the spring arm, this operation is to be discussed in further detail hereinafter.

The mounting apparatus of the present invention comprises a stationary base 40. The base 40 is meant to be attached to a mounting surface such as a tabletop. It is preferably to be attached by vacuum means and in this regard it is noted that in, for example, FIG. 2 that there is some type of a vacuum diaphragm 42 operated from the operating lever 44.

The base 40 supports a swivel joint 46 having an aperture for receiving the bottom end 48 of the main support bar 50. The end 48 is substantially straight and then extends into a hook portion 52 the shape of which is most clearly illustrated in FIG. 3. The main support bar 50 also has a substantially straight and horizontal top end 54 for supporting the clamp 56.

The lower swivel joint 46 has associated therewith a tightening clamp 47 that is adapted to maintain the main support bar 50 in some predetermined position. The swivel 46 permits universal movement of the main support bar 50 relative to the base 40. In a particular preferred position of the main support bar, it is noted that it is substantially vertical as viewed in FIG. 2 and is furthermore positioned so that preferably the upper member 14 is horizontal or close to horizontal as illustrated in FIG. 3. In this regard it is furthermore noted that the hooked portion 52 of the main support bar 50 is configured so that the support base 40 is disposed directly under the articulator as viewed in particular in FIGS. 2 and 3. Reference is now made to FIGS. 4 and 5 that show further details of the clamp 56. As illustrated in FIG. 5 the clamp 56 has a generally C-shaped cross section and is adapted to have a slot therein received by the rear portion of the upper member 14. A set screw 60 attaches the clamp 56 to the end 54 of the main support bar 50. A thumb screw 62 secures the clamp and thus the entire mounting apparatus to the upper member 14 of the articulator.

Once the base 40 is in place, and the swivel 46 is furthermore locked in place, then the articulator upper member 14 is held in a fixed position by means of the clamp 56.

Intermediate the ends of the main support rod 50, there is supported the adjustable spring mount 66. As indicated in FIG. 3, the mount 66 is preferably supported at the straight section at the end 48 of the main support bar 50. To secure the amount 66 to the end 48 there is provided a thumb screw 68. In this regard please refer to FIGS. 6-8 wherein there is illustrated the mount 66 and the securing thumb screw 68.

The mount 66 supports a torsion spring 70 by means of spring supports 72 received in holes in the mount 66 and secured by means of screws 74.

The torsion spring 70 in turn supports a spring arm 78 that is of triangular configuration as illustrated in FIG. 6. The spring arm 78 may have a covering sleeve 80 at the apex thereof where contact occurs with the lower member 12 of the articulator.

It is noted that the spring arm 78 extends through the torsion spring and has a threaded end 82 for receiving the thumb screw 84. It is furthermore noted that the torsion spring 70 has an end 86 disposed about the spring arm 78 such as illustrated in FIGS. 6 and 7 so as to bias the spring arm 78 to an upper pivoting position as indicated by the arrow 88 in FIG. 7.

As indicated previously, the spring arm 78 has associated therewith a thumb screw 84. When the thumb screw 84 is tightened this clamps the spring arm tight against the ends of the torsion spring 70 and in this way maintains the spring arm in a fixed position. Alternatively, when the thumb screw 84 is not secured against the torsion spring then the spring arm 78 provides a predetermined force upwardly for providing limited support at the more forward end of the articulator lower member 12.

With regard to the positioning of the lower member 12 by the spring arm 78, reference is made to FIG. 3 which shows the spring arm in solid in an uppermost position bearing against the underside surface of the member 12 and also shows the spring arm 78 in phantom in a lower position. The spring arm may be secured in either of these positions by tightening up the thumb screw 84.

As indicated previously, the mounting apparatus of the present invention maintains the articulator upper member 14 stationary and the support provided by the spring arm 78 enables the articulator lower member 12 to be maintained in a number of different predetermined positions. This enables accurate simulation of lower jaw movements such as the left excursion indicated by movement of the lower cast in the direction of arrow 35 in FIG. 2. The spring arm 78 may be locked in a number of different positions so as to provide different height wise positions of the articulator lower member 12 and thus different height wise positions of the lower cast relative to the upper cast. A thumb screw of the spring arm 78 may be tightened in any one of these desired positions and then the operator can move the articulator lower member 12 laterally under thumb pressure in either direction to then simulate lower jaw movement. The lateral movement is controlled not only by the support underneath but also by the interaction at the articulator itself in particular between the condyles and their associated guides.

Having now described one embodiment of the present invention it should now be apparent to those skilled in the art that numerous other embodiments are contemplated as falling within the scope of the present invention. For example, one form of clamp has been shown for clamping the mounting apparatus of the articulator upper member. However, it is understood that other forms of the clamp may also be employed depending upon the particular state-of-the-art articulator with which the apparatus is used. Also, although not described in complete detail herein, it is understood that the apparatus of the present invention enables use of the articulator to carry out all forms of operation whether it be in connection with diagnostic and planning sequences or in constructing prostheses or other restorative appliances. In this regard the fixing of the spring arm enables precise centric alignment and precise setting of the gap between the casts.

What is claimed is:

1. A mounting apparatus for a dental articulator having an upper member for supporting an upper dental cast, a lower member for supporting a lower dental cast and pivot means enabling pivotal and lateral relative movement between the upper and lower members, said mounting apparatus comprising;

a stationary base, a rigid support member having a lower end supported from the stationary base and having an upper end, a clamp means for releaseably receiving and supporting the articulator upper member, said clamp means disposed at the upper end of the rigid support member and adapted to hold the articulator upper member in a stationary position relative to the base, an adjustable support piece, means for supporting the adjustable support piece from the rigid support member intermediate the ends thereof, said adjustable support piece having means for contacting the articulator lower member to limit the lowermost position thereof while permitting at least lateral movement of the articulator lower member relative to the articulator upper member to thus simulate human jaw movements, said lower member includes a mounting base and said means for contacting the articulator lower member includes a support arm engaging said mounting base, said rigid support member being hook-shaped with the stationary base disposed under the articulator lower member.

2. A mounting apparatus as set forth in claim 1 wherein said stationary base has a swivel means for supporting the lower end of the rigid support member.

3. A mounting apparatus as set forth in claim 2 wherein said stationary base has vacuum means for fixedly securing the base to a support surface.

4. A mounting apparatus as set forth in claim 3 including a base clamp for clamping the rigid support member in one of a number of different possible positions on the stationary base.

5. A mounting apparatus as set forth in claim 1 wherein said rigid support member has a lower end that is connected to the stationary base through a swivel means and an upper end that is disposed substantially horizontally where attached to the clamp means.

6. A mounting apparatus as set forth in claim 1 wherein the support bar extends at the rear of the articulator and said support arm engaging the underside of said mounting base.

7. A mounting apparatus as set forth in claim 6 wherein the means for supporting the adjustable support piece includes a support piece mount secured from the angularly disposed lower end of the rigid support member.

8. A mounting apparatus as set forth in claim 7 wherein said clamp means includes a C-shaped piece for receiving the articulator upper member.

9. A mounting apparatus as set forth in claim 8 including releaseable securing means for the clamp means.

10. A mounting apparatus for a dental articulator having an upper member for supporting an upper dental cast, a lower member for supporting a lower dental cast and pivot means enabling pivotal and lateral relative movement between the upper and lower members, said mounting apparatus comprising;
   a stationary base,
   a rigid support member having a lower end supported from the stationary base and having an upper end,
   a clamp means for releaseably receiving and supporting the articulator upper member,
   said clamp means disposed at the upper end of the rigid support member and adapted to hold the articulator upper member in a stationary position relative to the base,
   an adjustable support piece,
   means for supporting the adjustable support piece from the rigid support member intermediate the ends thereof,
   said adjustable support piece having means for contacting the articulator lower member to limit the lowermost position thereof while permitting at least lateral movement of the articulator lower member relative to the articulator upper member to thus simulate human jaw movements,
   said adjustable support piece comprising a support arm pivotally attached to the means for supporting the adjustable support piece.

11. A mounting apparatus as set forth in claim 10 wherein the support arm has an outer free end that contacts the underside of the articulator lower member.

12. A mounting apparatus as set forth in claim 11 wherein said support arm has a spring support.

13. A mounting apparatus as set forth in claim 12 wherein said support arm is V-shaped.

14. A mounting apparatus as set forth in claim 11 including means for releaseably securing the support arm in a fixed position.

15. A mounting apparatus as set forth in claim 14 wherein said means for releaseably securing includes a thumb screw.

16. A mounting apparatus for a dental articulator having an upper member for supporting an upper dental cast, a lower member for supporting a lower dental cast and pivot means enabling pivotal and lateral relative movement between the upper and lower members, said mounting apparatus comprising;
   a stationary base,
   a rigid support member having a lower end supported from the stationary base and having an upper end,
   a clamp means for releaseably receiving and supporting the articulator upper member,
   said clamp means disposed at the upper end of the rigid support member and adapted to hold the articulator upper member in a stationary position relative to the base,
   an adjustable support piece,
   means for supporting the adjustable support piece from the rigid support member intermediate the ends thereof,
   said adjustable support piece having means for contacting the articulator lower member to limit the lowermost position thereof while permitting at least lateral movement of the articulator lower member relative to the articulator upper member to thus simulate human jaw movement,
   said lower member has a mounting base and said means for contacting the articulator lower member includes a support arm engaging said mounting base,
   said adjustable support piece further having means for securing said means for contacting the articulator lower member in a number of different positions correspnding to different desired positioning of the articulator lower member.

* * * * *